United States Patent
Jäger et al.

Patent Number: 4,988,383
Date of Patent: Jan. 29, 1991

[54] FUNGICIDAL AND PLANT GROWTH-REGULATING CYCLOPROPYL-HYDROXYETHYL-AZOLYL-DERIVATIVES

[75] Inventors: Gerhard Jäger; Udo Kraatz, both of Leverkuse; Stefan Dutzmann, Duesseldorf; Wilhelm Brandes, Leichlingen; Gerd Hänssler, Leverkusen, all of Fed. Rep. of Germany

[73] Assignee: Bayer Aktiengesellschaft, Leverkusen, Fed. Rep. of Germany

[21] Appl. No.: 475,640

[22] Filed: Feb. 6, 1990

[30] Foreign Application Priority Data

Feb. 21, 1989 [DE] Fed. Rep. of Germany ....... 3905316

[51] Int. Cl.$^5$ .................. A01N 43/653; C07D 249/08
[52] U.S. Cl. ............................................ 71/92; 71/76; 548/101; 548/267.8; 548/268.6; 514/184; 514/383
[58] Field of Search ...................... 71/92, 76; 548/101, 548/267.8, 268.6; 514/184, 383

[56] References Cited

U.S. PATENT DOCUMENTS

4,723,984  2/1988  Holmwood et al. .................. 71/76

FOREIGN PATENT DOCUMENTS

0297383  1/1989  European Pat. Off.

*Primary Examiner*—Mary C. Lee
*Assistant Examiner*—Patricia L. Morris
*Attorney, Agent, or Firm*—Sprung, Horn, Kramer & Woods

[57] ABSTRACT

Fungicidal and plant growth-regulating cyclopropyl-hydroxyethyl-azolyl-derivatives of the formula

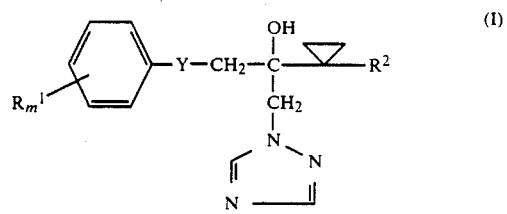

in which
$R^1$ represents halogen, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 halogen atoms, halogenalkoxy having 1 or 2 carbon atoms and 1 to 5 halogen atoms, halogenoalkylthio having 1 or 2 carbon atoms and 1 to 5 halogen atoms, alkoximinomethyl having 1 to 4 carbon atoms in the alkoxy group, phenyl optionally substituted by alkyl having 1 to 2 carbon atoms and/or halogen or phenoxy optionally substituted by alkyl having 1 or 2 carbon atoms and/or halogen, m represents the numbers 0, 1, 2 or 3, $R^2$ represents optionally substituted benzyl or the radical —COOR$^3$, in which
  $R^3$ represents alkyl, optionally substituted phenyl or optionally substituted benzyl,
and
Y represents oxygen or sulphur,
and their acid addition salts and metal salt complexes.

12 Claims, No Drawings

FUNGICIDAL AND PLANT GROWTH-REGULATING CYCLOPROPYL-HYDROXYETHYL-AZOLYL-DERIVATIVES

The present invention relates to new cyclopropyl-hydroxyethyl-azolyl derivatives, a process for their preparation and their use as fungicides and plant growth regulators.

It has already been disclosed that numerous hydroxyalkyl-azolyl derivatives possess fungicidal and plant growth-regulating properties (compare EP-OS 0,040,345 and EP-OS 0,297,383). The activity of these substances is very good; however, the activity at low application rates in some cases leaves something to be desired.

New cyclopropyl-hydroxyethyl-azolyl- derivatives of the formula

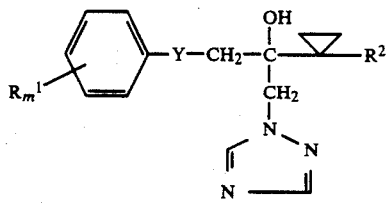

in which
R¹ represents halogen, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 halogen atoms, halogenoalkoxy having 1 or 2 carbon atoms and 1 to 5 halogen atoms, halogenoalkylthio having 1 or 2 carbon atoms and 1 to 5 halogen atoms, alkoximinomethyl having 1 to 4 carbon atoms in the alkoxy group, phenyl optionally substituted by alkyl having 1 or 2 carbon atoms and/or halogen or phenoxy optionally substituted by alkyl having 1 or 2 carbon atoms and/or halogen, m represents the numbers 0, 1, 2 or 3,
R² represents optionally substituted benzyl or the radical —COOR³, in which
R³ represents alkyl, optionally substituted phenyl or optionally substituted benzyl,
and
Y represents oxygen or sulphur,
and their acid addition salts and metal salt complexes have now been found.

The substances according to the invention contain an asymmetrically substituted carbon atom. They may therefore be obtained in the form of optical isomers. The invention relates both to the individual isomers and to their mixtures.

Furthermore, it has been found that cyclopropyl-hydroxyethyl-azolyl derivatives of the formula (I) and their acid addition salts and metal salt complexes are obtained when oxiranes of the formula

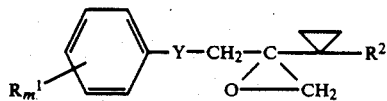

in which

R¹, R², Y and m have the abovementioned meanings, are reacted with 1,2,4-triazole of the formula

in the presence of an acid-binding agent and in the presence of a diluent,
and, if desired, an acid or a metal salt is then adducted to the compounds of the formula (I) thus obtained.

Finally, it has been found that the new cyclopropyl-hydroxyethyl-azolyl derivatives of the formula (I) and their acid addition salts and metal salt complexes possess strong fungicidal and plant growth-regulating properties.

Surprisingly, the substances according to the invention possess a better fungicidal and plant growth-regulating activity than the most similar previously known compounds in terms of constitution having the same type of action.

Formula (I) provides a general definition of the hydroxyethyl-azolyl derivatives according to the invention. Preferably, in this formula, R¹ represents fluorine, chlorine, bromine, methyl, ethyl, isopropyl, tert.-butyl, methoxy, methylthio, trifluoromethyl, trifluoromethoxy, trifluoromethylthio, methoximinomethyl, phenyl optionally substituted by fluorine, chlorine and/or methyl or phenoxy optionally substituted by fluorine, chlorine and/or methyl, m represents the numbers 0, 1, 2 or 3,
R² represents benzyl which is optionally monosubstituted to trisubstituted in the phenyl moiety by identical or different substituents from the group consisting of halogen, halogenoalkyl having 1 or 2 carbon atoms and 1 to 5 halogen atoms, alkyl having 1 to 4 carbon atoms and alkoxy having 1 to 4 carbon atoms, or
R² represents the radical of the formula —COOR³, in which
R³ represents alkyl having 1 to 4 carbon atoms, phenyl optionally substituted by halogen and/or alkyl having 1 to 4 carbon atoms or benzyl optionally substituted by halogen and/or alkyl having 1 to 4 carbon atoms,
and
Y represents oxygen or sulphur.

Particularly preferred compounds of the formula (I) are those in which
R¹ represents fluorine, chlorine, bromine, methyl, ethyl, isopropyl, tert.-butyl, methoxy, methylthio, trifluoromethyl, trifluoromethoxy, trifluoromethylthio, methoximinomethyl, phenyl optionally substituted by fluorine, chlorine and/or methyl or phenoxy optionally substituted by fluorine, chlorine and/or methyl,
m represents the numbers 0, 1, 2 or 3,
R² represents benzyl which is optionally monosubstituted or disubstituted in the phenyl moiety by identical or different substituents from the group consisting of fluorine, chlorine, bromine, trifluoromethyl, methyl, ethyl, methoxy and ethoxy, or
R² represents the radical of the formula —COOR³, in which R³ represents methyl, ethyl, n-propyl, isopropyl, n-butyl, tert.-butyl, phenyl optionally substituted by fluorine, chlorine and/or methyl or benzyl optionally substituted by fluorine, chlorine and/or methyl, and Y represents oxygen or sulphur.

Preferred compounds according to the invention are also addition products of acids and those cyclopropyl-hydroxyethyl-azolyl derivatives of the formula (I), in which R¹, R², Y and m have the meanings which have already been mentioned as preferred for these radicals or this index.

The acids which can be adducted preferably include hydrohalic acids, such as, for example, hydrochloric acid and hydrobromic acid, in particular hydrochloric acid, and further phosphoric acid, nitric acid, sulphuric acid, mono- and bifunctional carboxylic acids and hydroxycarboxylic acids, such as, for example, acetic acid, maleic acid, succinic acid, fumaric acid, tartaric acid, citric acid, salicylic acid, sorbic acid and lactic acid and sulphonic acids, such as, for example, p-toluene sulphonic acid, 1,5-naphthalenedisulphonic acid or camphor sulphonic acid.

In addition, preferred compounds according to the invention are addition products of salts of metals of main groups II to IV and subgroups I and II and also IV to VIII of the Periodic Table of the elements and those cyclopropyl-hydroxyethyl-azolyl derivatives of the formula (I), in which R¹, R², Y and m have the meanings which have already been mentioned as preferred for these radicals and this index.

In this connection, the salts of copper, zinc, manganese, magnesium, tin, iron and nickel are particularly preferred. Possible anions of these salts are those which are derived from those acids which lead to physiologically tolerable addition products. In this connection, particularly preferred acids of this type are the hydrohalic acids, such as, for example, hydrochloric acid and hydrobromic acid, and in addition phosphoric acid, nitric acid and sulphuric acid.

If 2-[1-(4-chloro-benzyl)-cyclopropyl]-2-(4-chloro-phenoxy-methyl)-oxirane and 1,2,4-triazole are used as starting substances, the course of the process according to the invention can be illustrated by the following equation:

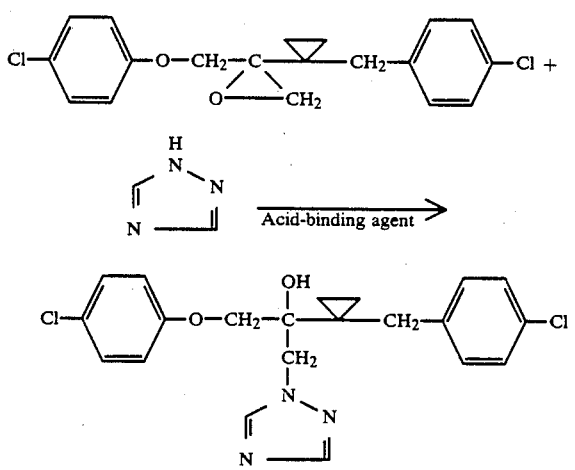

Formula (II) provides a general definition of the oxiranes required as starting substances in the process according to the invention. In this formula, R¹, R², Y and m preferably have those meanings which have already been mentioned as preferred for these radicals and for this index in connection with the description of the substances of the formula (I) according to the invention.

The oxiranes of the formula (II) were hitherto undisclosed. They can be prepared by a process in which (a) Cyclopropyl ketones of the formula

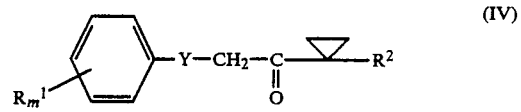

in which

R¹, R², Y and m have the abovementioned meanings, are reacted either (α) with dimethyloxosulphonium methylide of the formula

or (β) with dimethylsulphonium methylide of the formula

in the presence of a diluent.

The cyclopropyl ketones of the formula (IV) required as starting substances in process (a) can be prepared by a process in which (b) halogeno ketones of the formula

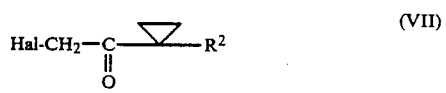

in which

R² has the abovementioned meaning and

Hal represents chlorine or bromine, are reacted with phenyl derivatives of the formula

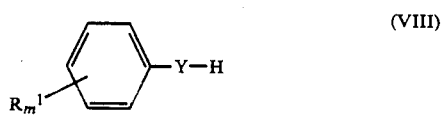

in which

R¹, Y and m have the abovementioned meanings, in the presence of an acid-binding agent and, if appropriate, in the presence of a diluent.

The halogeno ketones of the formula (VII) required as starting substances in process (b) can be prepared by a process in which (c) ketones of the formula

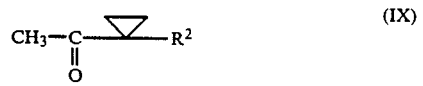

in which $R^2$ has the abovementioned meaning,
are reacted with chlorinating agents or brominating agents in the presence of a diluent.

The ketones of the formula (IX) required as starting substances in process (c) are known or can be synthesized by methods which are known in principle (compare Synthesis 1977. 189).

Possible chlorinating agents and brominating agents for process (c) are all chlorinating and brominating reagents which are customary for reactions of this type. Preferably, sulfuryl chloride, sulfuryl bromide, chlorine and bromine can be used.

Possible diluents for process (c) are all inert organic solvents which are customary for reactions of this type. Preferably, halogenated aliphatic hydrocarbons, such as methylene chloride, chloroform and carbon tetrachloride, can be used.

The reaction temperatures can be varied within a certain range in process (c). In general, the reaction is carried out at temperatures between $-10°$ C. and $+60°$ C., preferably between $0°$ C. and $+40°$ C.

When carrying out process (c), the reaction is in general carried out under normal pressure, as in the other processes described in this application. However, it is also possible in each case to work under elevated or reduced pressure.

When carrying out process (c), in general a stoichiometric amount or even a small excess of chlorinating or brominating agent is employed per mol of ketone of the formula (IX). Working up is carried out by customary methods. In general, a procedure is used in which the reaction mixture is washed successively with dilute aqueous sodium hydrogen carbonate solution and water, then dried and concentrated.

Formula (VIII) provides a general definition of process (b). In this formula, $R^1$, Y and m preferably have those meanings which have already been mentioned as preferred for these radicals and for this index in connection with the description of the substances of the formula (I) according to the invention. The phenyl derivatives of the formula (VIII) are generally known compounds of organic chemistry.

Possible acid-binding agents for carrying out process (b) are all customary acid acceptors. Preferably, alkali metal carbonates and hydrogen carbonates, such as sodium carbonate, potassium carbonate and sodium hydrogen carbonate, further alkali metal hydroxides and alkoxides such as sodium hydroxide, potassium hydroxide, sodium methoxide or potassium tert.-butoxide, in addition tertiary aliphatic or aromatic amines, such as triethylamine, N,N-dimethyl-cyclohexyl-amine, N,N-dimethylbenzylamine and pyridine, and in addition cyclic amines, such as 1,5-diaza-bicyclo[4.3.0]non-5-ene (DBN), 1,8-diaza-bicyclo[5.4.0]undec-7-ene (DBU) and 1,4-diazabicyclo[2.2.2]octane (DABCO) can be used.

Possible diluents for carrying out process (b) are all inert organic solvents. Preferably, aliphatic and aromatic, optionally halogenated hydrocarbons such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers such as diethyl ether and dibutyl ether, glycol dimethyl ether and diglycol dimethylether, tetrahydrofuran and dioxane, ketones such as acetone, methyl ethyl ketone, methyl isopropyl ketone and methyl isobutyl ketone, esters such as methyl acetate and ethyl acetate, nitriles such as, for example acetonitrile and propionitrile and pyridine, and also strongly polar solvents, such as dimethylformamide and dimethyl sulphoxide can be used.

The reaction temperatures in process (b) can be varied within a relatively large range. In general, the reaction is carried out at temperatures between $0°$ C. and $150°$ C., preferably between $20°$ C. and $130°$ C.

When carrying out process (b), in general 1 to 1.5 mole(s) of phenyl derivative of the formula (VIII) and 1 to 2 mole(s) of acid-binding agent are employed per mole of halogeno ketone of the formula (VII). Working up is carried out by customary methods. In general, a procedure is used in which, if appropriate after previously filtering off deposited salts, the reaction mixture is concentrated, the residue is taken up in an organic solvent which is poorly miscible with water, and the resulting solution is washed, dried and then concentrated.

The dimethyl-oxo-sulphonium methylide of the formula (V) required as a reaction component in process (a) is known (compare J. Am. Chem. Soc. 87, 1363–1364 (1965)). It is processed in the above reaction in the freshly prepared state by generating it in situ by reaction of trimethyloxosulphonium iodide with sodium hydride or sodium amide, potassium tert.-butoxide or sodium methoxide, in the presence of a diluent.

The dimethylsulphonium methylide of the formula (VI) additionally possible as a reaction component in process (a) is also known (compare Heterocycles 8, 397 (1977)). It is also employed in the above reaction in the freshly prepared state by generating it in situ, for example, from trimethylsulphonium halide or trimethylsulphonium methylsulphate, in the presence of a strong base, such as, for example, sodium hydride, sodium amide, sodium methoxide, potassium tert.-butoxide or potassium hydroxide, in the presence of a diluent, such as tert.-butanol or dimethyl sulphoxide.

Possible diluents for carrying out process (a) are inert organic solvents. Preferably, alcohols, such as tert.-butanol, ethers, such as tetrahydrofuran or dioxane, further aliphatic and aromatic hydrocarbons, such as benzene, toluene or xylene, and strongly polar solvents, such as dimethyl sulphoxide or acetonitrile can be used.

The reaction temperatures when carrying out process (a) can be varied within a relatively large range. In general, the reaction is carried out between $0°$ C. and $100°$ C., preferably between $10°$ C. and $60°$ C.

When carrying out a process (a), in general 1 to 3 mole(s) of dimethyloxosulphonium methylide of the formula (V) or dimethylsulphonium methylide of the formula (VI) are employed per mole of cyclopropyl ketone of the formula (IV). The isolation of the oxiranes of the formula (II) is carried out by customary methods.

Possible acid-binding agents for carrying out the process according to the invention are all customary acid acceptors. Preferably, all those acid-binding agents which have preferably been mentioned in connection with the description of process (b) can be used.

Possible diluents for carrying out the process according to the invention are all customary inert organic solvents. Preferably nitriles, such as, in particular, acetonitrile; aromatic hydrocarbons, such as benzene, toluene and dichlorobenzene; formamides, such as, in particular, dimethylformamide, and also hexamethylphosphoramide, can be used.

The reaction temperatures can be varied within a relatively large range when carrying out the process according to the invention. In general, the reaction is carried out at temperatures between 0° C. and 200° C., preferably between 50° C. and 150° C.

When carrying out the process according to the invention, 1 to 4 mole(s) of 1,2,4-triazole of the formula (III) and 1 to 2 mole(s) of base are preferably employed per mole of oxirane of the formula (II). The isolation of the final products is carried out in a customary manner.

The cyclopropyl-hydroxyethyl-azolyl derivatives of the formula (I) obtainable by the process according to the invention can be converted into acid addition salts or metal salt complexes.

For the preparation of acid addition salts of the compounds of the formula (I), suitable acids are preferably those which have already been mentioned as preferred acids in connection with the description of the acid addition salts according to the invention. formula (I) can be obtained in a simple manner by customary salt formation methods, for example by dissolving a compound of the formula (I) in a suitable inert solvent and adding the acid, for example hydrochloric acid, and can be isolated in a known manner, for example by filtering off, and, if necessary, can be purified by washing with an inert organic solvent.

For the preparation of metal salt complexes of the compounds of the formula (I), suitable salts of metals are preferably those which have already been mentioned as preferred metal salts in connection with the description of the metal salt complexes according to the invention.

The metal salt complexes of the compounds of the formula (I) can be obtained in a simple manner by customary methods, such as, for example, by dissolving the metal salt in alcohol, for example ethanol, and adding to compounds of the formula (I). Metal salt complexes can be isolated in a known manner, for example by filtering off, and can be purified, if necessary, by recrystallization.

The active compounds according to the invention have a strong microbicidal action and can be employed as fungicides.

Fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal and bacterial diseases which come under the generic names listed above may be mentioned as examples, but not by way of limitation:

Xanthomonas species, such as *Xanthomonas oryzae*;
Pseudomonas species, such as *Pseudomonas lachrymans*;
Erwinia species, such as *Erwinia amylovora*;
Pythium species, such as *Pythium ultimum*;
Phytophthora species, such as *Phytophthora infestans*;
Pseudoperonospora species such as *Pseudoperonospora humuli* or *Pseudoperonospora cubense*;
Plasmopara species, such as *Plasmopara viticola*;
Peronospora species, such as *Peronospora pisi* or *P. brassicae*;
Erysiphe species, such as *Erysiphe graminis*;
Sphaerotheca species, such as *Sphaerotheca fuliginea*;
Podosphaera species, such as *Podosphaera leucotricha*;
Venturia species, such as *Venturia inaequalis*;
Pyrenophora species, such as *Pyrenophora teres* or *P. graminea*; (conidia form: Drechslera, syn: Helminthosporium);
Cochliobolus species, such as *Cochliobolus sativus*; (conidia form: Drechslera, syn: Helminthosporium);
Uromyces species, such as *Uromyces appendiculatus*;
Puccinia species, such as *Puccinia recondita*;
Tilletia species, such as *Tilletia caries*;
Ustilago species, such as *Ustilago nuda* or *Ustilago avenae*;
Pellicularia species, such as *Pellicularia sasakii*;
Pyricularia species, such as *Pyricularia oryzae*;
Fusarium species, such as *Fusarium culmorum*;
Botrytis species, such as *Botrytis cinerea*;
Septoria species, such as *Septoria nodorum*;
Leptosphaeria species, such as *Leptosphaeria nodorum*;
Cercospora species, such as *Cercospora canescens*;
Alternaria species, such as *Alternaria brassicae* and
Pseudocercosporella species, such as *Pseudocercosporella herpotrichoides*.

The good toleration, by plants, of the active compounds, at the concentrations required for combating plant diseases, permits treatment of above-ground parts of plants, of vegetative propagation stock and seeds, and of the soil.

The active compounds according to the invention are particularly suitable for combating cereal and rice diseases, such as rust, mildew, *Cochiobolus sativus*, *Pyrenophora teres* and *Leptosphaeria nodorum* in cereals, or *Pyricularia oryzae* in rice. They can further be used against Sphaerotheca on cucumbers.

In addition, the active compounds according to the invention also possess plant growth-regulating properties.

The active compounds according to the invention engage in the metabolism of plants and can therefore be employed as growth regulators.

Experience to date of the mode of action of plant growth regulators has shown that an active compound can also exert several different actions on plants. The actions of the compounds depend essentially on the point in time at which they are used, relative to the stage of development of the plant, and on the amounts of active compound applied to the plants or their environment and the way in which the compounds are applied. In each case, growth regulators are intended to influence the crop plants in the particular manner desired.

Plant growth-regulating compounds can be employed, for example, to inhibit vegetative growth of the plants. Such inhibition of growth is, inter alia, of economic interest in the case of grasses, since it is thereby possible to reduce the frequency of cutting the grass in ornamental gardens, parks and sports grounds, on verges, at airports or in fruit orchards. The inhibition of growth of herbaceous and woody plants on verges and in the vicinity of pipelines or overland lines or, quite generally, in areas in which heavy additional growth of plants is undesired, is also of importance.

The use of growth regulators to inhibit the growth in length of cereals is also important. The danger of bending ("lodging") of the plants before harvesting is thereby reduced or completely eliminated. Furthermore, growth regulators can strengthen the stem of cereals, which again counteracts lodging. Use of growth regulators for shortening and strengthening the stem enables higher amounts of fertilizer to be applied to increase the yield, without danger of the cereal lodging.

In the case of many crop plants, inhibition of the vegetative growth makes denser planting possible, so that higher yields per area of ground can be achieved. An advantage of the smaller plants thus produced is also that the crop can be worked and harvested more easily.

Inhibition of the vegetative growth of plants can also lead to increases in yield, since the nutrients and assimilates benefit blossoming and fruit formation to a greater extent than they benefit the vegetative parts of plants.

Promotion of vegetative growth can also frequently be achieved with growth regulators. This is of great utility if it is the vegetative parts of the plants which are harvested. Promoting the vegetative growth can, however, also simultaneously lead to a promotion of generative growth, since more assimilates are formed, so that more fruit, or larger fruit, is obtained.

Increases in yield can in some cases be achieved by affecting the plant metabolism, without noticeable changes in vegetative growth. A change in the composition of plants, which in turn can lead to a better quality of the harvested products, can furthermore be achieved with growth regulators. Thus it is possible, for example, to increase the content of sugar in sugar beets, sugar cane, pineapples and citrus fruit or to increase the protein content in soy beans or cereals. Using growth regulators it is desired constituents, such as, for example, sugar in sugar beets or sugar cane, before or after harvesting. It is also possible favourably to influence the production or the efflux of secondary plant constituents. The stimulation of latex flux in rubber trees may be mentioned as an example.

Parthenocarpous fruit can be formed under the influence of growth regulators. Furthermore, the gender of the flowers can be influenced. Sterility of the pollen can also be produced, which is of great importance in the breeding and production of hybrid seed.

Branching of plants can be controlled by using growth regulators. On the one hand, by breaking the apical dominance the development of side shoots can be promoted, which can be very desirable, especially in the cultivation of ornamental plants, also in connection with growth inhibition. On the other hand, however, it is also possible to inhibit the growth of side shoots. There is great interest in this action, for example, in the cultivation of tobacco or in the planting of tomatoes.

The amount of leaf on plants can be controlled, under the influence of growth regulators, so that defoliation of the plants at a desired point in time is achieved. Such defoliation is of great importance in the mechanical harvesting of cotton, but is also of interest for facilitating harvesting in other crops, such as, for example, in viticulture. Defoliation of the plants can also be carried out to lower the transpiration of plants before they are transplanted.

The shedding of fruit can also be controlled with growth regulators. On the one hand, it is possible to prevent premature shedding of fruit. However, on the other hand, shedding of fruit, or even the fall of blossom, can be promoted up to a certain degree ("thinning out") in order to interrupt the alternance. By alternance there is understood the peculiarity of some varieties of fruit to produce very different yields from year to year, for endogenic reasons. Finally, using growth regulators it is possible to reduce the force required to detach the fruit at harvest time so as to permit mechanical harvesting or facilitate manual harvesting.

Using growth regulators, it is furthermore possible to achieve an acceleration or retardation of ripening of the harvest product, before or after harvesting. This is of particular advantage, since it is thereby possible to achieve optimum adaptation to market requirements. Furthermore, growth regulators can at times improve the coloration of fruit. In addition, concentrating the ripening within a certain period of time is also achievable with the aid of growth regulators. This provides the preconditions for being able to carry out complete mechanical or manual harvesting in only a single operation, for example in the case of tobacco, tomatoes or coffee.

Using growth regulators, it is furthermore possible to influence the latent period of seeds or buds of plants, so that the plants, such as, for example, pineapple or ornamental plants in nurseries, germinate, shoot or blossom at a time at which they normally show no readiness to do so. Retarding the shooting of buds or the germination of seeds with the aid of growth regulators can be desirable in regions where frost is a hazard, in order to avoid damage by late frosts.

Finally, the resistance of plants to frost, drought or a high salt content in the soil can be induced with growth regulators. Cultivation of plants in regions which are usually unsuitable for this purpose thereby becomes possible.

The active compounds can be converted into the customary formulations, such as solutions, emulsions, suspensions, powders, foams, pastes, granules, aerosols, very fine capsules in polymeric substances and in coating compositions for seed, as well as ULV formulations.

These formulations are produced in a known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water. By liquefied gaseous extenders or carriers are meant liquids which are gaseous at ambient temperature and under atmospheric pressure, for example aerosol propellants, such as halogenated hydrocarbons as well as butane, propane, nitrogen and carbon dioxide. As solid carriers there are suitable: for example, ground natural minerals, such as kaolins, clays, talc, chalk, quartz, attapulgite, montmorillonite or diatomaceous earth, and ground synthetic minerals, such as highly-disperse silica, alumina and silicates. As solid carriers for granules there are suitable: for example, crushed and fractionated natural minerals such as calcite, marble, pumice, sepiolite and dolomite, as well as synthetic granules of inorganic and organic meals, and granules of organic material such as sawdust, coconut shells, corn cobs and tobacco stalks. As emulsifying and/or foam-forming agents there are suitable: for example, non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albuxin hydrolysis products. As dispersing agents there are suitable: for example lignin-sulphite waste liquors and methylcellulose.

Adhesives such as carboxymeth-ylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in the formulations as a mixture with other known active compounds, such as fungicides, insecticides, acaricides and herbicides, and also as mixtures with fertilizers and other growth regulators.

The active compounds can be used as such, in the form of their formulations or as the use forms prepared therefrom, such as ready-to-use solutions, emulsifiable concentrates, emulsions, foams, suspensions, wettable powders, pastes, soluble powders, dusting agents and granules. They are used in the customary manner, for example by watering, spraying, atomizing, scattering, dusting, foaming, coating and the like. Furthermore, it is possible to apply the active compounds in the ultralow volume process or to inject the active compound preparation or the active compound itself into the soil. It is also possible to treat the seeds of plants.

When the substances according to the invention are used as fungicides, the amount applied can be varied within a relatively large range depending on the type of application. Thus the active compound concentrations in the use forms in the treatment of parts of plants are in general between 1 and 0.0001% by weight, preferably between 0.5 and 0.001%. In the treatment of seed, in general active compound amounts of 0.001 to 50 g per kilogram of seed, preferably 0.01 to 10 g, are required. In the treatment of the soil, active compound concentrations of 0.00001 to 0.1% by weight, preferably 0.0001 to 0.02% by weight, are necessary at the site of action.

When the compounds according to the invention are used as plant growth regulators, the amounts applied can be varied within a relatively large range. In general, 0.01 to 50 kg, preferably 0.05 to 10 kg, of active compound are used per hectare of soil surface.

When these substances according to the invention are used as plant growth regulators, the rule is that the application is carried out in a preferred period of time, the exact definition of which depends on the climatic and vegetative circumstances.

The preparation and the use of the active compounds according to the invention follows from the following examples.

PREPARATION EXAMPLES

EXAMPLE 1

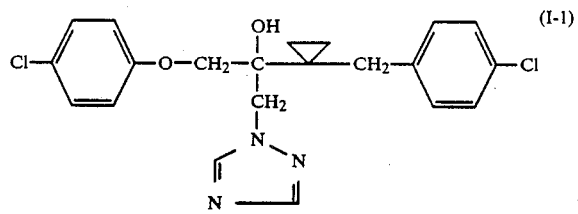

28 g (0.08 mol) of 2-(4-chlorophenoxymethyl)-2-(4-chlorobenzyl-cycloprop-1-yl)-oxirane are added to a suspension of 13.4 g (0.2 mol) of 1,2,4-triazole and 26.7 g (0.2 mol) of potassium carbonate in 150 ml of dimethylformamide and the mixture is heated with stirring to 90° C. After stirring for 16 hours, the dimethylformamide is largely removed under reduced pressure at 45° C. and the residue is treated with methylene chloride/water. The organic phase is separated off, washed twice with water, dried over magnesium sulphate and concentrated under reduced pressure. The residue is recrystallized from isopropanol.

Yield: 23 g (70% of theory) m.p. 155° C.

Preparation of starting substances:

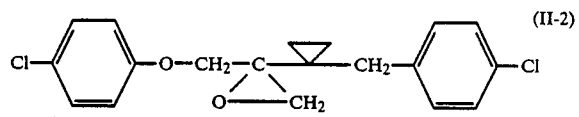

21 g (0.17 mol) of dimethyl sulphate are added dropwise with stirring at 20° C. to a solution of 10.5 g (0.17 mol) of dimethyl sulphide in 100 ml of acetonitrile. After standing for 2 days at 20° C., 9.2 g (0.17 mol) of sodium methoxide is added to this solution, the mixture is stirred for 30 minutes at 20° C. and then 29 g (0.09 mol) of 4-chlorophenoxymethyl 1-(4-chlorobenzyl)cycloprop-1-yl ketone are added. After stirring for 16 hours at 20° C., the reaction mixture is poured into water and the mixture is extracted with methylene chloride. The organic phase is washed with water, dried over magnesium sulphate and concentrated under reduced pressure. 25.2 g (80% of theory) of 2-(4-chlorophenoxymethyl)-2-[(4-chlorobenzyl)cycloprop-1-yl]-oxirane are obtained in the form of a colorless oil which is employed for further synthesis without additional purification.

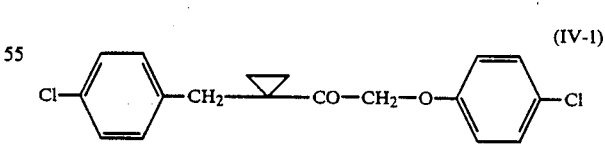

26 1 g (0.09 mol) of 1-(4-chlorobenzyl)-1-bromoacetyl-cyclopropane are added dropwise with stirring at 20° C. to a solution of 11.6 g (0.09 mol) of 4-chlorophenol and 12.4 g (0.09 mol) of potassium carbonate in 150 ml of acetone. After heating for 16 hours under reflux, the inorganic constituents are filtered off. The filtrate is concentrated under reduced pressure, and the residue is taken up using water/methylene chloride. The organic phase is washed twice with 1N sodium hydroxide solution and concentrated under reduced pressure. 4-chlorophenoxymethyl 1-(4-chlorobenzyl)-cycloprop-1-yl ketone is obtained as a viscous oil which is reacted without further purification.

Yield: 27.4 g (91% of theory).

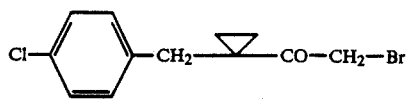
(VII-1)

48 g (0.3 mol) of bromine are added dropwise at −10° C. to a solution of 62.6 g (0.3 mol) of 1-(4-chlorobenzyl)-1-acetyl-cyclopropane in 200 ml of methanol in such a way that decolorization always occurs. The mixture is then stirred for a further hour at 20° C., poured into 600 ml of water and extracted with methylene chloride. The organic phase is washed with water, dried over magnesium sulphate and concentrated under reduced pressure. 81.8 g of 1-(4-chlorobenzyl)-1-bromoacetylcyclopropane are thus obtained in the form of an oily liquid. The yield accordingly works out to be 95% of theory. The product is used for further synthesis without additional purification.

EXAMPLE 2

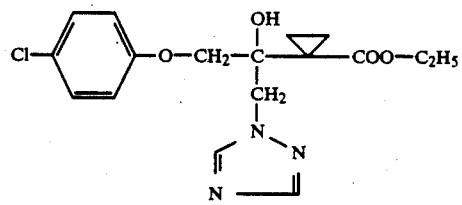
(I-2)

5.4 g (0.077 mol) of 1,2,4-triazole and 20.8 g (0.07 mol) of 2-[(4-chlorophenoxy)-methyl]-2-(1-ethoxycarbonyl-cycloprop-1-yl)-oxirane are added to a solution of 1.6 g (0.07 mol) of sodium in 10 ml of butanol. After boiling for 14 hours under reflux, the solvent is removed under reduced pressure and the residue is taken up using methylene chloride/water. The organic phase is separated off, dried over magnesium sulphate and concentrated under reduced pressure. The residue is chromatographed on silica gel using chloroform.

Yield: 8.6 g (33.6% of theory) m.p. 56°–58° C.

Preparation of starting substances:

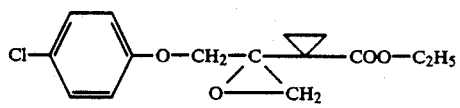
(II-2)

3.6 g (0.13 mol) of 80% strength sodium hydride are added under an argon atmosphere and with stirring at 10° to 20° C. to a suspension of 24 g (0.11 mol) of trimethylsulphoxonium iodide in 100 ml of dimethyl sulphoxide. After stirring for 30 minutes at 20° C., 17.1 g (0.061 mol) of 4-chlorophenoxymethyl 1-ethoxycarbonylcycloprop-1-yl ketone are added. The mixture is warmed to 60° C. for 1 hour. After this, the mixture is poured into 300 ml of water and extracted with methylene chloride. The combined organic extracts are washed with water, dried over magnesium sulphate and concentrated. 14 g (77.8% of theory) of 2-[(4-chlorophenoxy)-methyl]-2-(1-ethoxycarbonyl-cycloprop-1-yl)-oxirane are obtained as an oil which is further reacted without additional purification.

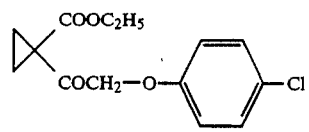
(IV-2)

47.2 g (0.2 mol) of ethyl 1-(bromoacetyl)-cyclopropanecarboxylate are added to a suspension of b 28 g (0.2 mol) of potassium carbonate and 26 g (0.2 mol) of 4-chlorophenol in 300 ml of acetone and the mixture is heated under reflux for 6 hours. Inorganic salts are then filtered off, the filtrate is concentrated under reduced pressure and the residue is distilled in vacuo. 39 g (69% of theory) of ethyl 1-(4-chlorophenoxyacetyl)-cyclopropanecarboxylate are obtained. B.P. 148°–150° C./0.45 mbar.

The substances of the formula

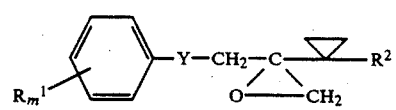
(II)

listed in the following Table I are also prepared according to the previously described methods.

TABLE 1

| Ex No. | Compound No. | $R_m^1$ | $R^2$ | Y | Melting point (°C.) |
|---|---|---|---|---|---|
| 3 | I-3 | 4-CH$_3$ | —CH$_2$—C$_6$H$_4$—Cl | O | 116 |
| 4 | I-4 | 4-Cl | —CH$_2$—C$_6$H$_5$ | O | 87 |
| 5 | I-5 | 4-Cl | —CH$_2$—C$_6$H$_3$Cl$_2$ | O | 118–123 |
| 6 | I-6 | 2-CH$_3$, 4-Cl | —CH$_2$—C$_6$H$_4$—Cl | O | 92 |
| 7 | I-7 | 4-F | —CH$_2$—C$_6$H$_4$—Cl | O | 125 |
| 8 | I-8 | 4-OCF$_3$ | —CH$_2$—C$_6$H$_4$—Cl | O | 123 |
| 9 | I-9 | 4-Br | —COO—C$_2$H$_5$ | O | 58–59 |
| 10 | I-10 | 4-F | —COO—C$_2$H$_5$ | O | 57–58 |
| 11 | I-11 | 2,4-Cl$_2$ | —CH$_2$—C$_6$H$_4$—Cl | O | 104 |

USE EXAMPLES

The compound indicated below was used as comparison substance in the following Examples:

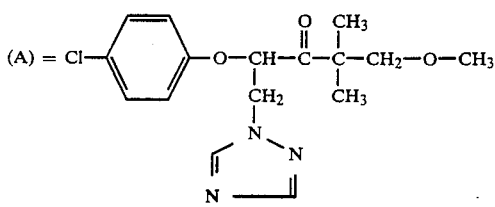

(A) = structure shown

EXAMPLE A

Erysiphe test (barley)/protective

Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are dusted with spores of *Erysiphe graminis f.sp. hordei*.

To test for curative activity, young plants are dusted with spores of *Erysiphe graminis f. sp. hordei*. 48 hours after the inoculation, the plants are sprayed with the preparation of active compound until dew-moist.

The plants are placed in a greenhouse at a temperature of about 20° C. and a relative atmospheric humidity of about 80%, in order to promote the development of powdery mildew pustules.

Evaluation is carried out 7 days after the inoculation.

Compounds (I-9) and (I-10) according to the invention show very good activity in this test.

EXAMPLE B

Pyrenophora teres test (barley)/protective

Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are sprayed with a conidia suspension of *Pyrenophora teres*. The plants then remain in an incubation cabin at 20° C. and 100% relative atmospheric humidity for 48 hours.

The plants are placed in a greenhouse at a temperature of about 20° C. and a relative atmospheric humidity of about 80%.

Evaluation is carried out 7 days after the inoculation.

Compound (I-2) according to the invention shows very good activity in this test.

EXAMPLE C

Venturia test (apple)/protective

Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous conidia suspension of the apple scab causative organism (*Venturia inaequalis*) and then remain in an incubation cabin at 20° C. and 100% relative atmospheric humidity for 1 day.

The plants are then placed in a greenhouse at 20° C. and a relative atmospheric humidity of about 70%.

Evaluation is carried out 12 days after the inoculation.

Compounds (I-2), (I-9) and (I-10) according to the invention show substantially better activity than the comparison substance (A) in this test.

EXAMPLE D

Pyricularia test (rice)/protective

Solvent: 12.5 parts by weight of acetone
Emulsifier: 0.3 parts by weight of alkylaryl polyglycol ether To produce a suitable preparation of active compound, 1 part by weight of active compound is mixed with the stated amount of solvent, and the concentrate is diluted with water and the stated amount of emulsifier to the desired concentration.

To test for protective activity, young rice plants are sprayed with the preparation of active compound until dripping wet. After the spray coating has dried on, the plants are inoculated with an aqueous spore suspension of Pyricularia oryzae. The plants are then placed in a greenhouse at 100% relative atmospheric humidity and 25° C.

Evaluation of the disease infestation is carried out 4 days after the inoculation.

Compounds (I-6), (I-8) and (I-9) according to the invention show very good activity in this test.

EXAMPLE E

Pyricularia test (rice)/systemic

Solvent: 12.5 parts by weight of acetone
Emulsifier: 0.3 parts by weight of alkylaryl polyglycol ether To produce a suitable preparation of active compound, 1 part by weight of active compound is mixed with the stated amount of solvent, and the concentrate is diluted with water and the stated amount of emulsifier to the desired concentration.

To test for systemic properties, standard soil in which young rice plants have been grown is watered with 40 ml of the preparation of active compound. 7 days after the treatment, the plants are inoculated with an aqueous spore suspension of Pyricularia oryzae. Thereafter, the plants remain in a greenhouse at a temperature of 25° C. and a relative atmospheric humidity of 100% until they are evaluated.

Evaluation of the disease infestation is carried out 4 days after the inoculation.

Compounds (I-2) and (I-10) according to the invention show very good activity in this test.

We claim:
1. A cyclopropyl-hydroxyethyl-azolyl derivative of the formula

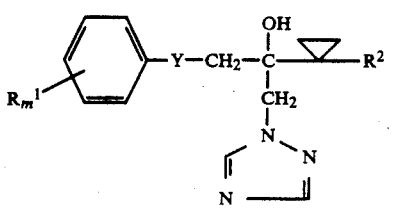

in which
R¹ represents halogen, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 halogen atoms, halogenoalkoxy having 1 or 2 carbon atoms and 1 to 5 halogen atoms, halogenoalkylthio having 1 or 2 carbon atoms and 1 to 5 halogen atoms, alkoximinomethyl having 1 to 4 carbon atoms in the alkoxy group, phenyl optionally substituted by alkyl having 1 or 2 carbon atoms and/or halogen or phenoxy optionally substituted by alkyl having 1 or 2 carbon atoms and/or halogen, m represents the numbers 0, 1, 2 or 3, R² represents benzyl which is optionally monosubstituted to trisubstituted in the phenyl moiety by identical or different substituents from the group consisting of halogen, halogenoalkyl having 1 or 2 carbon atoms and 1 to 5 halogen atoms, alkyl having 1 to 4 carbon atoms and alkoxy having 1 to 4 carbon atoms, or R² represents the radical of the formula —COOR³, in which
R³ represents alkyl having 1 to 4 carbon atoms, phenyl optionally substituted by halogen and/or alkyl having 1 to 4 carbon atoms or benzyl optionally substituted by halogen and/or alkyl having 1 to 4 carbon atoms, and Y represents oxygen or sulphur, or an addition product thereof with an acid or metal salt.

2. A cyclopropyl-hydroxyethyl-azolyl derivative or addition product thereof according to claim 1, in which R¹ represents fluorine, chlorine, bromine, methyl, ethyl, isopropyl, tert.-butyl, methoxy, methylthio, trifluoromethyl, trifluoromethoxy, trifluoromethylthio, methoximinomethyl, phenyl optionally substituted by fluorine, chlorine and/or methyl or phenoxy optionally substituted by fluorine, chlorine and/or methyl, m represents the numbers 0, 1, 2 or 3, R² represents benzyl which is optionally monosubstituted to trisubstituted in the phenyl moiety by identical or different substituents from the group consisting of halogen, halogenoalkyl having 1 or 2 carbon atoms and 1 to 5 halogen atoms, alkyl having 1 to 4 carbon atoms and alkoxy having 1 to 4 carbon atoms, or R² represents the radical of the formula —COOR³, in which
R³ represents alkyl having 1 to 4 carbon atoms, phenyl optionally substituted by halogen and/or alkyl having 1 to 4 carbon atoms or benzyl optionally substituted by halogen and/or alkyl having 1 to 4 carbon atoms, and Y represents oxygen or sulphur.

3. A cyclopropyl-hydroxyethyl-azolyl derivative or addition product thereof according to claim 1, in which R¹ represents fluorine, chlorine, bromine, methyl, ethyl, isopropyl, tert.-butyl, methoxy, methylthio, trifluoromethyl, trifluoromethoxy, trifluoromethylthio, methoximinomethyl, phenyl optionally substituted by fluorine, chlorine and/or methyl or phenoxy optionally substituted by fluorine, chlorine and/or methyl, m represents the numbers 0, 1, 2 or 3, R² represents benzyl which is optionally monosubstituted or disubstituted in the phenyl moiety by identical or different substituents from the group consisting of fluorine, chlorine, bromine, trifluoromethyl, methyl, ethyl, methoxy and ethoxy, or R² represents the radical of the formula —COOR³, in which
R³ represents methyl, ethyl, n-propyl, isopropyl, n-butyl, tert.-butyl, phenyl optionally substituted by fluorine, chlorine and/or methyl or benzyl optionally substituted by fluorine, chlorine and/or methyl, and Y represents oxygen or sulphur.

4. A compound according to claim 1, wherein such compound is 1-(4-chlorophenoxymethyl)-2-(1,2,4-triazol-1-yl) -1-(ethoxycarbonyl-cyclopropyl)-ethanol of the formula

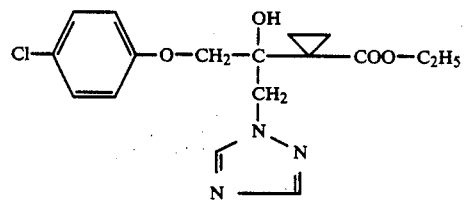

or an addition product thereof with an acid or metal salt.

5. A compound according to claim 1, wherein such compound is 1-(4-bromophenoxymethyl)-2-(1,2,4-triazol-1-yl)-1-(ethoxycarbonyl-cyclopropyl)-ethanol of the formula

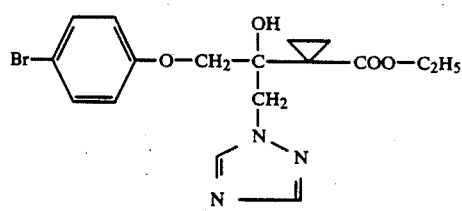

or an addition product thereof with an acid or metal salt.

6. A compound according to claim 1, wherein such compound is 1-(4-fluorophenoxymethyl)-2-(1,2,4- triazol-1-yl)-1-(1-ethoxycarbonyl-cyclopropyl)-ethanol of the formula

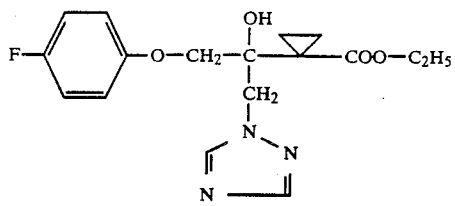

or an addition product thereof with an acid or metal salt.

7. A fungicidal composition comprising a fungicidally effective amount of a compound or addition product thereof according to claim 1 and an inert.

8. A method of combatting fungi which comprises applying to such fungi or to a fungus habitat a fungicidally effective amount or a compound or addition product thereof according to claim 1.

9. The method according to claim 8 wherein such compound is
1-(4-chlorophenoxymethyl)-2-(1,2,4-triazol-1-yl)-1-(ethoxycarbonyl-cyclopropyl)-ethanol,
1-(4-bromophenoxymethyl)-2-(1,2,4-triazol-1-yl)-1-(ethoxycarbonyl-cyclopropyl)-ethanol or
1-(4-fluorophenoxymethyl)-2-(1,2,4-triazol-1-yl)-1-ethoxycarbonyl-cyclopropy)-ethanol,
or an addition product thereof with an acid or metal salt.

10. A plant growth-regulating composition comprising a plant growth-regulating effective amount of a compound or addition product thereof according to claim 1 and an inert diluent.

11. A method of regulating the growth of plants which comprises applying to such plants or to a locus in which such plants are growing or are to be grown a plant growth-regulating effective amount of a compound or addition product thereof according to claim 1 and an inert diluent.

12. The method according to claim 10 wherein such compound is
1-(4-chlorophenoxymethyl)-2-(1,2,4-triazol-1-yl)-1-(ethoxycarbonyl-cyclopropyl)-ethanol,
1-(4-bromophenoxymethyl)-2-(1,2,4-triazol-1-yl)-1-(ethoxycarbonyl-cyclopropyl)-ethanol or
1-(4-fluorophenoxymethyl)-2-(1,2,4-triazol-1-yl)-1-(1-ethoxycarbonyl-cyclopropyl)-ethanol,
or an addition product thereof with an acid or metal salt.

* * * * *